United States Patent
Boyd et al.

(10) Patent No.: US 8,915,888 B2
(45) Date of Patent: Dec. 23, 2014

(54) DOSING AND DRIVE MECHANISM FOR DRUG DELIVERY DEVICE

(75) Inventors: Malcolm Boyd, Leamington Spa (GB); Richard Letham, Kingston Upon Thames (GB); David Plumptre, Worcestershire (GB); Robert Veasey, Leamington Spa (GB); James May, Earlsdon (GB); Matthew Jones, Warwickshire (GB); Samuel Ghazaros, Bristol (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 943 days.

(21) Appl. No.: 12/466,581

(22) Filed: May 15, 2009

(65) Prior Publication Data

US 2010/0094205 A1    Apr. 15, 2010

Related U.S. Application Data

(63) Continuation of application No. PCT/EP2007/009673, filed on Nov. 8, 2007.

(30) Foreign Application Priority Data

Nov. 17, 2006  (EP) .................................... 06023961

(51) Int. Cl.
*A61M 5/315*    (2006.01)
*A61M 5/30*    (2006.01)

(52) U.S. Cl.
CPC ....... *A61M 5/31595* (2013.01); *A61M 5/31585* (2013.01); *A61M 2005/31506* (2013.01); *A61M 5/31505* (2013.01); *A61M 5/31555* (2013.01)
USPC ............................ 604/208; 604/218; 604/224

(58) Field of Classification Search
CPC ..................... A61M 5/31583; A61M 5/31578; A61M 5/3155; A61M 5/31595; A61M 5/31548; A61M 5/31585; A61M 5/31555; A61M 5/31525; A61M 5/31526; A61M 5/315
USPC ............. 604/68–72, 131, 181, 187, 207–211, 604/224, 228
See application file for complete search history.

(56) References Cited

U.S. PATENT DOCUMENTS

| | | | |
|---|---|---|---|
| 4,568,335 A | 2/1986 | Updike et al. | |
| 4,592,745 A | 6/1986 | Rex et al. | |
| 7,517,334 B2 * | 4/2009 | Jacobs et al. | 604/110 |

(Continued)

FOREIGN PATENT DOCUMENTS

FR    2 612 782 A1    9/1988
WO    99/38554 A1    8/1999

(Continued)

OTHER PUBLICATIONS

International Search Report Form PCT/ISA210 (second sheet) (Apr. 2005)—PCT/EP2007/009673.

*Primary Examiner* — Matthew F Desanto
(74) *Attorney, Agent, or Firm* — McDonnell Boehnen Hulbert & Berghoff LLP

(57) ABSTRACT

The present invention relates to drive mechanisms suitable for use in drug delivery devices, in particular pen-type injectors, wherein a number of pre-set doses of medicinal product can be administered. In particular, the present invention relates to such drug delivery devices where a user may activate the drug delivery device.

20 Claims, 8 Drawing Sheets

(56) References Cited

U.S. PATENT DOCUMENTS

| | | | |
|---|---|---|---|
| 7,678,084 B2 * | 3/2010 | Judson et al. ............... 604/187 |
| 2004/0210199 A1 | 10/2004 | Atterbury et al. | |

FOREIGN PATENT DOCUMENTS

| | | |
|---|---|---|
| WO | 01/89613 A1 | 11/2001 |
| WO | 03/008023 A1 | 1/2003 |
| WO | 2004/078239 A1 | 9/2004 |
| WO | WO 2004078239 * | 9/2004 |
| WO | 2006/084876 A1 | 8/2006 |
| WO | 2006/089734 A1 | 8/2006 |
| WO | 2006/089768 A1 | 8/2006 |
| WO | WO 2006089734 * | 8/2006 |
| WO | 2008/058665 A1 | 5/2008 |

* cited by examiner

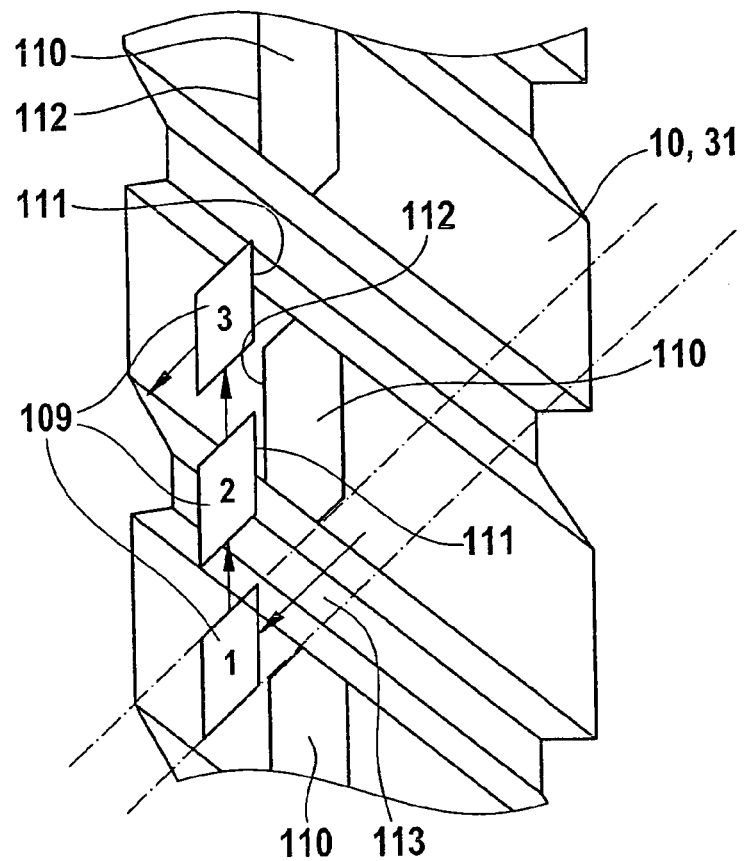
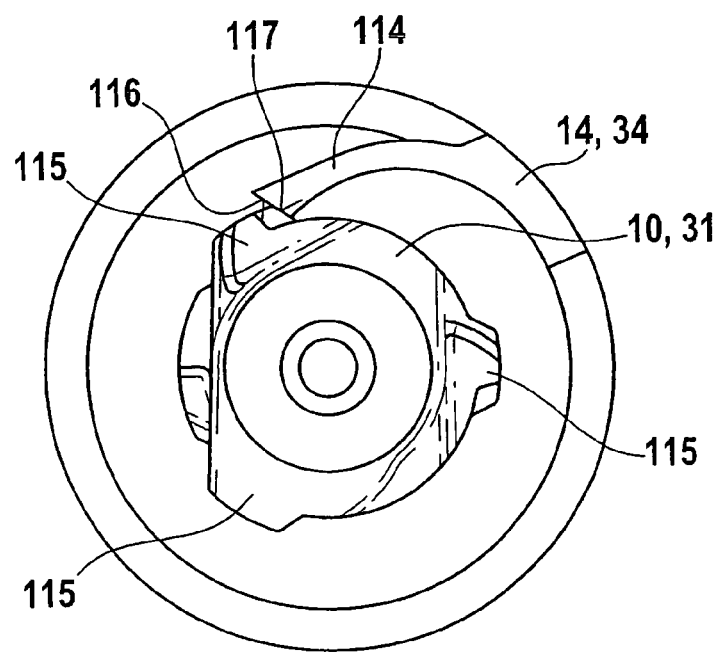

DOSING AND DRIVE MECHANISM FOR DRUG DELIVERY DEVICE

THE TECHNICAL FIELD OF THE INVENTION

The present invention relates to drive mechanisms suitable for use in drug delivery devices, in particular pen-type injectors, wherein a number of pre-set doses of medicinal product can be administered. In particular, the present invention relates to such drug delivery devices where a user may activate the drug delivery device.

DESCRIPTION OF RELATED ART

Such drug delivery devices have application where persons without formal medical training, i.e., patients, need to administer an accurate and predefined dose of a medicinal product, such as heparin or insulin. In particular, such devices have application where medicinal product is administered on an irregular basis over a short-term or long-term period.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. Where the device is to be disposable rather than reusable, the device should be cheap to manufacture and easy to dispose of (preferably being suitable for recycling). To meet these requirements the number of parts required to assemble the device and the number of material types the device is made from need to be kept to a minimum.

User operated drug delivery devices are well known within the medical field.

U.S. Pat. No. 6,048,336 discloses an injection device wherein a pre-selected set medicinal dose to be administered is selected by means of a rotatable dosing element. Once the dose has been set, an end member is pulled axially away from the remainder of the pen base until a stop is reached. A dose is dispensed by the end member being axially driven towards the pen base in turn driving an internal plunger-engaging member. Whilst this device provides a useful embodiment for administering a pre-set dose the intuitiveness of setting a pre-set dose remains unsolved as two actions need to be performed to arm the device.

WO 2004/078239 A1 teaches a drug delivery device having a clutch means located between the dose dial sleeve and the drive sleeve and in which when the dose dial sleeve and the drive sleeve are coupled, both are allowed to rotate with respect to the housing and when the dose dial sleeve and the drive sleeve are de-coupled, rotation of the dose dial sleeve with respect to the housing is allowed, whilst rotation of the drive sleeve with respect to the housing is not allowed, whereby axial movement of the drive sleeve is allowed so that a force is transferred in the longitudinal direction to the proximal end of the drug delivery device.

In WO 2003/020347 A2 a medication dispensing apparatus is divulged having an axially moving actuator that is pulled out of the device body to set a dose and pushed into the body to dispense the set dose, having a clutch element with a number of prongs used to selectively transmit motion of the actuator member to the drive member.

Surprisingly it was found that the drive mechanism according to instant invention without having a clutch element provides a valuable technical alternative for push-pull drive mechanisms, wherein reduced force is needed to actuate the mechanism. This is achieved by the introduction of a piston rod as defined by instant invention. Further the drive mechanism according to instant invention further provides the advantage of intuitive and easy to use dose setting.

DESCRIPTION OF THE INVENTION

According to a first aspect of the present invention, a drive mechanism for use in a drug delivery device comprising:
  a housing having a proximal and distal end;
  a non-rotatable drive sleeve;
  a piston rod engaged with the said drive sleeve optionally by engagement means; characterized in that,
  a) when the said drive sleeve moves proximally with respect to the said housing the said piston rod does not move with respect to the said housing;
  b) when the said drive sleeve moves distally the said piston rod rotates with respect to the said housing so that a force is transferred in the longitudinal direction to the distal end of the said drug delivery device.

In a preferred embodiment of the drive mechanism of instant invention the said drive mechanism comprises a piston rod comprising a distal threaded portion threadedly engaged with the said housing and an "engagement means" located at the proximal end of the said piston rod for releasable engagement to the said drive sleeve.

In another preferred embodiment of the drive mechanism of instant invention the engagement means of the piston rod consists of one or more flexible regions.

In a further preferred embodiment of the drive mechanism of instant invention the engagement means of the piston rod consists of a unidirectional rotational coupling.

The term "drug delivery device" according to instant invention shall mean a single-dose or multi-dose or pre-set dose or pre-defined dose, disposable or re-useable device designed to dispense a user selectable or pre-defined dose of a medicinal product, preferably multiple pre-defined doses, e.g. insulin, growth hormones, low molecular weight heparins, and their analogues and/or derivatives etc. Said device may be of any shape, e.g. compact or pen-type. Dose delivery may be provided through a mechanical (optionally manual) drive mechanism or electrical drive mechanism or electro-mechanical mechanism or stored energy drive mechanism, such as a spring, etc. Dose selection may be provided through a manual mechanism or electro-mechanical mechanism or electronic mechanism. Additionally, said device may contain components designed to monitor physiological properties such as blood glucose levels, etc. Furthermore, the said device may comprise a needle or may be needle-free. In addition, the said device may comprise a fixed needle or a replaceable needle or a moving needle or a shielded moving needle. In particular, the term "drug delivery device" shall mean a disposable needle-based pen-type device providing multiple pre-defined doses having mechanical and manual dose delivery and dose selection mechanisms, which is designed for use by persons without formal medical training such as patients. Preferably, the drug delivery device is of the injector-type.

The term "housing" according to instant invention shall preferably mean any exterior housing ("main housing", "body", "shell") or interior housing ("insert", "inner body") having a helical thread. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge, which may be replaceable or non-replaceable, from which a number of doses of a medicinal product may by dispensed.

In a more specific embodiment of instant invention, the housing is provided with a plurality of dose stops adapted to be abutted by a radial and/or axial stop provided on the drive sleeve. Preferably, at least one of the dose stops comprises a biasing stop located between the drive sleeve and the housing.

The term "engaged" according to instant invention shall particularly mean the interlocking of two or more components of the drive mechanism/drug delivery device, e.g. a spline, thread, or meshed teeth connection, preferably the interlocking of helical threads of components ("threadedly engaged").

The term "drive sleeve" according to instant invention shall mean any essentially tubular component of essentially circular cross-section and which is further releasably connected to the piston rod. The said drive sleeve may be of a unitary or multi-part construction.

In a more particular embodiment of instant invention, the drive sleeve is provided at the proximal end with a user activation means. In a more specific embodiment the user activation means consists of ribbed surfaces designed to enable the user to grip the drive sleeve securely when setting the device and a smooth concave surface designed to provide a comfortable means of dispensing the device.

The term "releasable engagement" according to instant invention shall preferably mean that two components of instant mechanism or device are joined for translation of force or movement in one direction only, preferably during dispense.

The term "piston rod" according to instant invention shall mean a component adapted to operate through/within the housing, designed to translate axial movement through/within the drug delivery device, preferably from the drive sleeve to the piston, for the purpose of discharging/dispensing an injectable product. Said piston rod may be flexible or not. It may be a simple rod, a lead-screw, a rack and pinion system, a worm gear system, or the like. It may further be of a unitary or multi-component construction. The term "piston rod" shall further mean a component having a circular or non-circular cross-section. It may be made of any suitable material known by a person skilled in the art.

In a preferred embodiment, the piston rod comprises at least one, more preferably two, external and/or internal helical threads (helical grooves). In another preferred embodiment of the piston rod according to instant invention, a first helical thread is located at the distal end and a second helical thread is located at the proximal end of the said piston rod, whereby the said threads may have the same or, preferably, opposite dispositions. In another preferred embodiment the piston rod of instant invention comprises threads having the same leads at the proximal and the distal end. In yet another preferred embodiment of instant invention the lead of the second helical thread of the piston rod shall be greater than the lead of the first helical thread. More preferred, the ratio of the leads of the helical threads of the said first and the said second helical threads is 1:1 to 1:20, even more preferred 1:1 to 1:10, most preferred 1:2. Preferably, one of the said threads is designed to engage with the drive sleeve.

Alternatively, in another preferred embodiment of the said piston rod of instant invention, the thread which engages with the drive sleeve is formed on a flexible region and/or regions of the said piston rod.

In yet another preferred embodiment of the said piston rod of instant invention a unidirectional rotational coupling means is provided between the proximal and distal threaded portions of the said piston rod.

In a preferred embodiment of the present invention the drive mechanism comprises non-return features which prevent rotation of the piston rod at least in one direction with respect to the housing when the drive sleeve moves proximally with respect to the housing. These non-return features preferably comprise an engaging feature which is designed to engage a stopping feature on the piston rod. This engaging feature can e.g. be at least one feature selected from the group consisting of a) at least one arm with a flexible section (and preferably a solid section) which is in constant engagement with a helical groove on the piston rod and which is designed to axially engage a step in the helical groove which is the stopping feature, b) at least one engaging element with a cross section of essentially a parallelogram in constant engagement with a helical groove on the piston rod which is designed to engage a section with a smaller helix angle (preferably a flat section) in the helical groove which is the stopping feature, c) at least one non-flexible engaging element which is connected to the drive sleeve which is designed to abut at least one of a plurality of raised sections on an outer surface of the piston rod which is the stopping feature, d) at least one ratchet arm which is connected to the drive sleeve or the housing and which is designed to engage at least one of a plurality of engaging sections (e.g. raised sections of edges of recesses) on an outer surface of the piston rod which is the stopping feature and e) at least one guiding feature of the drive sleeve which is designed to longitudinally guide a raised element on the outer surface of the piston rod which is the stopping feature.

The term "unidirectional rotational coupling means" according to instant invention shall mean two interfacing co-located surfaces having features that are designed to allow transmission of torque and/or rotation in one direction only.

The term "flexible region" according to instant invention shall mean any compliant and/or elastic and/or pivotable element of any component designed to deflect and/or move when subjected to a force. In a preferred embodiment, the said flexible region may be one or more cantilevers. In another preferred embodiment, the said flexible region may be one or more flexible arms.

The term "helical thread" according to instant invention shall preferably mean a full or part thread, e.g., a cylindrical spiral rib/groove, located on the internal and/or external surface of a component of the drug delivery device, having an essentially triangular or square or rounded section designed to allow continuous free rotation and/or axial movement between components. Optionally, a thread may be further designed to prevent rotational and/or axial movement of certain components in one direction.

The term "graphical status indicator" according to instant invention shall preferably mean any markings, symbols, numerals, etc., e.g. printed on the external surface of a component of the device, for example the drive sleeve or an odometer or a dose dial sleeve, or the like, preferably the drive sleeve, for indicating to the user when the device has been activated and/or is in operation and/or the direction of operation and/or a dose of medicament has been delivered.

The "distal end" of the device or a component of the device shall mean the end, which is closest to the dispensing end of the device.

The term "proximal end" of the device or a component of the device shall mean the end, which is furthest away from the dispensing end of the device.

The term "flexible" shall mean that a flexible component can be deformed elastically by a force exerted on the component during normal use of the drive mechanism and will therefore return to its original relaxed form as soon as the force is removed. The term "non-flexible" shall mean that a non-flexible component is not deformed by a force exerted on the component during the normal use of the drive mechanism.

A second aspect of instant invention provides an assembly for use in a drug delivery device comprising the drive mechanism according to instant invention.

A third aspect of the present invention provides a drug delivery device comprising the drive mechanism or the assembly according to instant invention.

A fourth aspect of the present invention provides a method of assembling a drug delivery device comprising the step of providing a drive mechanism or an assembly according to instant invention.

A fifth aspect of instant invention is the use of a drug delivery device according to instant invention for dispensing a medicinal product preferably dispensing a pharmaceutical formulation (e.g. solution, suspension etc.) comprising an active compound for example selected from the group consisting of insulin, growth hormone, low molecular weight heparin, their analogues and their derivatives.

BRIEF DESCRIPTION OF THE DRAWINGS

Without any limitation, the instant invention will be explained in greater detail below in connection with a preferred embodiment and with reference to the drawings in which:

FIG. 7 shows schematically a third design of non-return features for a drive mechanism according to the present invention;

FIGS. 8a and 8b show schematically a fourth design of non-return features for a drive mechanism according to the present invention.

DETAILED DESCRIPTION OF THE EMBODIMENTS

Example 1

Figure 1:
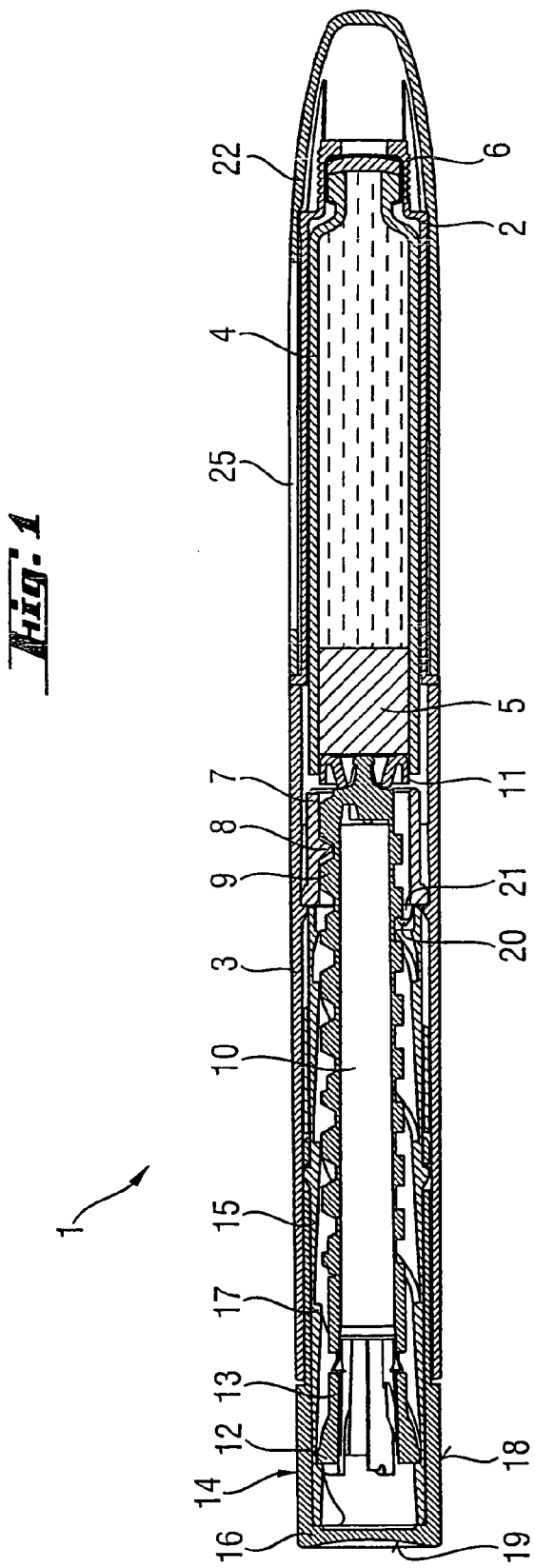
FIG. 1 shows a sectional view of a first embodiment of the drug delivery device in accordance with the present invention in a first, cartridge full, position.
Figure 2:
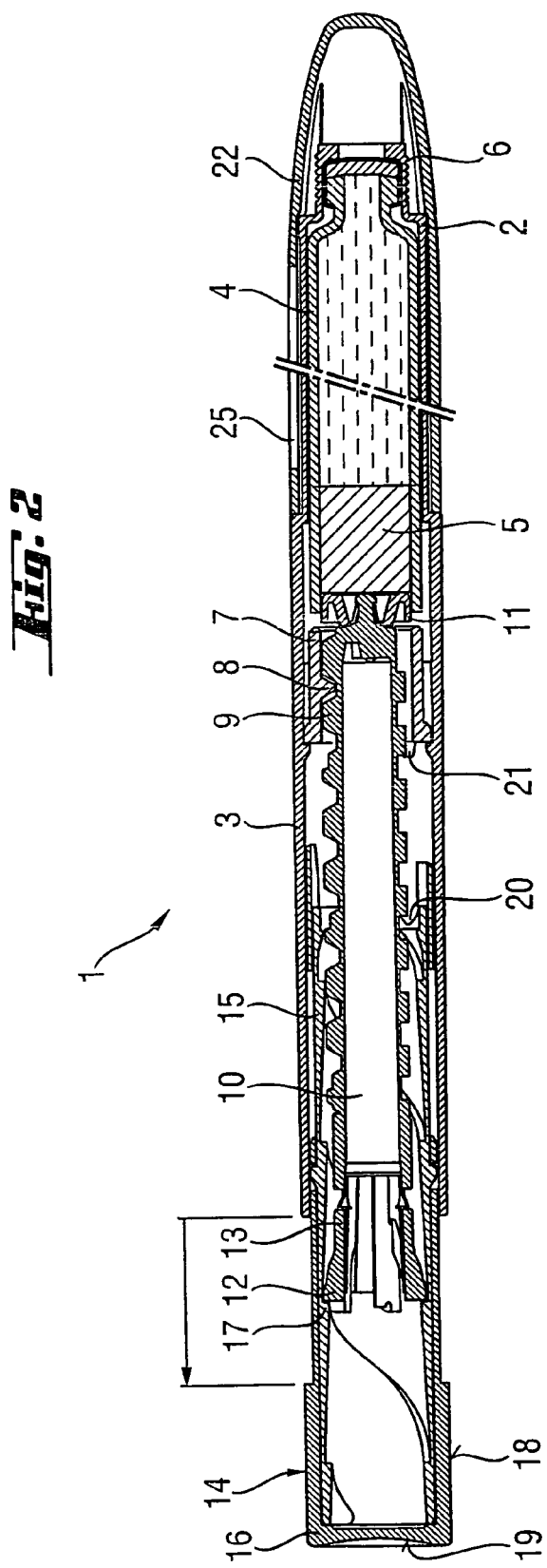
FIG. 2 shows a sectional view of a first embodiment of the drug delivery device in accordance with the present invention in a second, first dose set, position.
Figure 3:
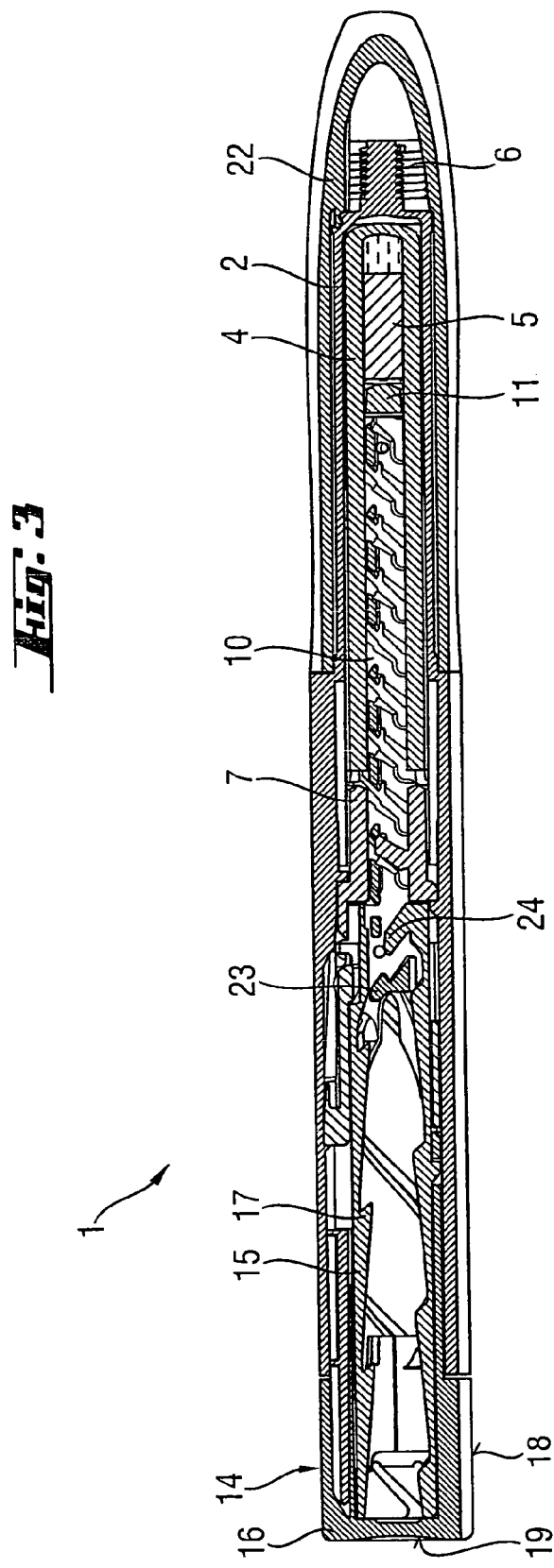
FIG. 3 shows a sectional view of a first embodiment of the drug delivery device in accordance with the present invention in a third, final dose dispensed, position.

Referring first to FIGS. 1 to 3, there is shown a drug delivery device in accordance with the present invention.

The drug delivery device (1) comprises a cartridge retaining part (2), and a main (exterior) housing part (3). The proximal end of the cartridge retaining part (2) and the distal end of the main housing (3) are secured together by any suitable means known to the person skilled in the art. In the illustrated embodiment, the cartridge retaining part (2) is secured within the distal end of the main housing part (3).

A cartridge (4) from which a number of doses of a medicinal product may be dispensed is provided in the cartridge retaining part (2). A piston (5) is retained in the proximal end of the cartridge (4).

A removable cap (22) is releasably retained over the distal end of the cartridge retaining part (2). The removable cap (22) is optionally provided with one or more window apertures through which the position of the piston (5) within the cartridge (4) can be viewed.

The distal end of the cartridge retaining part (2) in the illustrated embodiment, is provided with a distal threaded region (6) designed for the attachment of a suitable needle assembly (not shown) to enable medicament to be dispensed from the cartridge (4).

In the illustrated embodiment, the main housing part (3) is provided with an internal housing (7). The internal housing (7) is secured against rotational and/or axial movement with respect to the main housing part (3). The internal housing (7) is provided with a threaded circular opening (8) extending through the distal end of the internal housing (7). In the illustrated embodiment the threaded circular opening (8) comprises a series of part threads rather than a complete thread. Alternatively, the internal housing (7) may be formed integrally with the main housing part (3). Additionally, the internal housing (7) is provided with a plurality of guide slots and pawl means.

A first thread (9) is formed at the distal end of the piston rod (10). The piston rod (10) is of generally circular cross-section. The first thread (9) of the piston rod (10) extends through and is threadedly engaged with the threaded circular opening (8) of the internal housing (7). A pressure foot (11) is located at the distal end of the piston rod (10). The pressure foot (11) is disposed to abut the proximal face of the piston (5). A second thread (12) is formed at the proximal end of the piston rod (10). In the illustrated embodiment the second thread (12) comprises a series of part threads, rather than a complete thread, formed on flexible arms (13) of the piston rod (10).

The first thread (9) and the second thread (12) are oppositely disposed.

In the illustrated embodiment the first thread (9) is provided with a plurality of features (not shown) that cooperate with the part threads of the threaded circular opening (8) to prevent movement of the piston rod (10) in the proximal direction during setting of the device.

A drive sleeve (14) extends about the piston rod (10). The drive sleeve (14) comprises a threaded part (15) of a generally cylindrical cross-section and an activation part (16). The threaded part (15) and the activation part (16) are secured to each other to prevent rotational and/or axial movement there between. Alternatively, the drive sleeve (14) may be a unitary component consisting of an integrated threaded part (15) and activation part (16).

In the illustrated embodiment, the threaded part (15) is provided with a longitudinally extending helical thread (17) formed on the internal cylindrical surface. The flank of the proximal side of the helical thread (17) is designed to maintain contact with the second thread (12) of the piston rod (10) when dispensing a dose, whilst the flank of the distal side of the helical thread (17) is designed to allow the second thread (12) of the piston rod (10) to disengage when setting a dose.

In this way the helical thread (17) of the threaded part (15) is releasably engaged with the second thread (12) of the piston rod (10).

The drive sleeve (14) has a plurality of features formed on the external surface designed to move axially within the guide slots of the internal housing (7). These guide slots define the extent of permissible axial movement of the drive sleeve (14) with respect to the housing part (3). In the illustrated embodiment the guide slots also prevent rotational movement of the drive sleeve (14) relative to the main housing part (3).

The activation part (16) of the drive sleeve (14) has a plurality of grip surfaces (18) and a dispensing face (19).

The drive sleeve (14) is provided with a detent means that is designed to interact with the pawl means of the internal housing (7).

To increase intuitiveness of the operation of the device, the main housing part (3) may be provided with a window aperture through which graphical status indicators, provided on the drive sleeve (14), can be viewed.

Operation of the drug delivery device in accordance with the present invention will now be described.

To set a dose a user grips the grip surfaces (18) of the drive sleeve (14). The user then pulls the drive sleeve (14) in a proximal direction away from the main housing part (3).

The piston rod (10) is prevented from moving proximally by the part threads of the threaded circular opening (8) of the internal housing (7) interacting with thread features on the first thread (9) of the piston rod (10) or by any other suitable means. As the drive sleeve (14) travels in the proximal direction relative to the piston rod (10), the second thread (12) of the piston rod (10) is displaced radially inwards by the flank of the distal side of helical thread (17) of the drive sleeve (14).

The proximal travel of the drive sleeve (14) is limited by the guide slots (not shown) of the internal housing (7) a distance corresponding to essentially one thread pitch of the helical thread (17) of the drive sleeve (14). At the end of the travel of the drive sleeve (14), the second thread (12) of the piston rod (10) engages with the helical thread (17) under the action of the flexible arms (13) of the piston rod (10). As indicated in FIG. 2, by this action the drive sleeve (14) is displaced a distance essentially equal to one pitch of the helical thread (17) of the drive sleeve (14) in the proximal direction relative to the piston rod (10). The action of the second thread (12) positively engaging the helical thread (17) of the drive sleeve (14) under a force provided by the flexible arms (13) creates an audible and tactile feedback to the user to indicate that the dose has been set. Additionally, visual feedback regarding dose setting may be indicated by an optional graphical status indicator, provided on the drive sleeve (14), which can be viewed through an optional window aperture in the main housing part (3).

When the dose has been set, the user may then dispense this dose by depressing the dispensing face (19) of the activation part (16) of the drive sleeve (14). By this action the drive sleeve (14) is moved axially in the distal direction relative to the main housing part (3). As the second thread (12) of the piston rod (10) is positively engaged with the helical thread (17) of the drive sleeve (14) the piston rod (10) is caused to rotate with respect to the internal housing (7) by the axial movement of the drive sleeve (14) in the distal direction. As the piston rod (10) rotates, the first thread (9) of the piston rod (10) rotates within the threaded circular opening (8) of the internal housing (7) causing the piston rod (10) to move axially in the distal direction with respect to the internal housing (7).

The distal axial movement of the piston rod (10) causes the pressure foot (11) to bear against the piston (5) of the cartridge (4) causing a dose of medicament to be dispensed through an attached needle.

The distal travel of the drive sleeve (14) is limited by the guide slots (not shown) of the internal housing (7). Audible and tactile feedback to indicate that the dose has been dispensed is provided by the interaction of the detent (not shown) of the drive sleeve (14) with the pawl means (not shown) of the internal housing (7). Additionally, visual feedback regarding dose dispensing may be indicated by an optional graphical status indicator, provided on the drive sleeve (14), which can be viewed through an optional window aperture in the main housing part (3).

Further doses may be delivered as required up to a predetermined maximum number of doses. FIG. 3 shows the drug delivery device of instant invention in a condition where the maximum number of doses has been delivered. In this condition lug features (23) on the piston rod (10) interlock with lug features (24) on the drive sleeve (14) to prevent further axial movement of the drive sleeve (14) in the proximal direction.

Example 2

Figure 4:
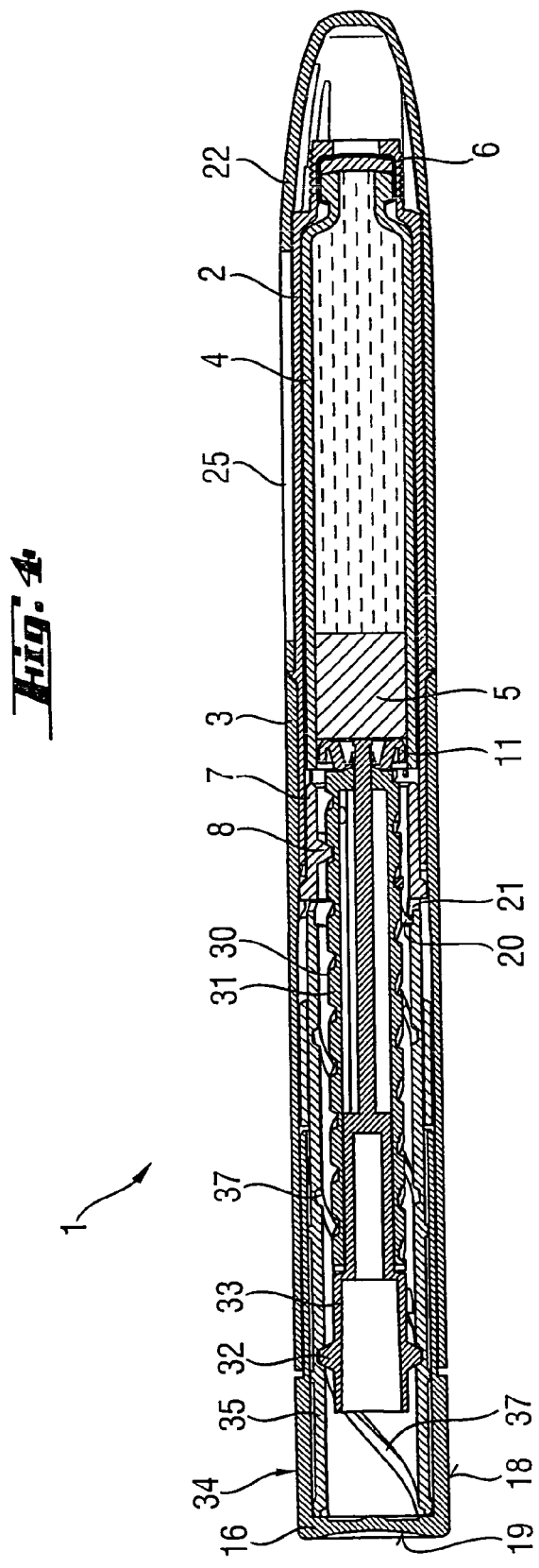
FIG. 4 shows a sectional view of a second embodiment of the drug delivery device in accordance with the present invention in a first, cartridge full, position.

Referring to FIG. 4, there is shown an alternative embodiment of the drug delivery device in accordance with the present invention.

It should be noted that in FIG. 4, components of example 2 that correspond to those of example 1 (FIGS. 1 to 3) utilise the same numbering system. New components are indicated by new numbers.

The drug delivery device (1) comprises a housing having a cartridge retaining part (2), and a main (exterior) housing part (3). The proximal end of the cartridge retaining part (2) and the distal end of the main housing (3) are secured together by any suitable means known to the person skilled in the art. In the illustrated embodiment, the cartridge retaining part (2) is secured within the distal end of the main housing part (3).

A cartridge (4) from which a number of doses of a medicinal product may be dispensed is provided in the cartridge retaining part (2). A piston (5) is retained in the proximal end of the cartridge (4).

A removable cap (22) is releasably retained over the distal end of the cartridge retaining part (2). The removable cap (22) is optionally provided with one or more window apertures (25) through which the position of the piston (5) within the cartridge (4) can be viewed.

The distal end of the cartridge retaining part (2) in the illustrated embodiment, is provided with a distal threaded region (6) designed for the attachment of a suitable needle assembly to enable medicament to be dispensed from the cartridge (4).

In the illustrated embodiment, the main housing part (3) is provided with an internal housing (7). The internal housing (7) is secured against rotational and/or axial movement with respect to the main housing part (3). The internal housing (7) is provided with a threaded circular opening (8) extending through the distal end of the internal housing (7). In the illustrated embodiment the threaded circular opening (8) comprises a series of part threads rather than a complete thread. Alternatively, the internal housing (7) may be formed integrally with the main housing part (3). Additionally, the internal housing (7) is provided with a plurality of guide slots and pawl means (21).

In the illustrated embodiment, a helical thread (30) is formed on the piston rod (31). The piston rod (31) is of generally circular cross-section. The helical thread (30) of the piston rod (31) extends through and is threadedly engaged with the threaded circular opening (8) of the internal housing (7). A pressure foot (11) is located at the distal end of the piston rod (31). The pressure foot (11) is disposed to abut the proximal face of the piston (5).

A helical thread (32) is formed on the unidirectional rotational coupling means (33). In the illustrated embodiment the helical thread (32) comprises a series of part threads, rather than a complete thread.

The unidirectional rotational coupling means (33) is coupled to the piston rod (31) such that relative rotation between the unidirectional rotational coupling means (33) and the piston rod (31) is allowed in one direction only. In the illustrated embodiment, limited relative axial movement is permitted between the unidirectional rotational coupling means (33) and the piston rod (31) to allow the unidirectional rotational coupling means (33) to disengage rotationally from the piston rod (31).

The helical thread (30) of the piston rod (31) and the helical thread (32) of the unidirectional rotational coupling means (33) are oppositely disposed.

In the illustrated embodiment the helical thread (30) of the piston rod (31) is provided with a plurality of features that cooperate with the part threads of the threaded circular opening (8) to prevent movement of the piston rod (31) in the proximal direction during setting of the device.

A drive sleeve (34) extends about the piston rod (31) and the unidirectional rotational coupling means (33). The drive sleeve (34) comprises a threaded part (35) of a generally cylindrical cross-section and an activation part (16). The threaded part (35) and the activation part (16) are secured to each other to prevent rotational and/or axial movement there between. Alternatively, the drive sleeve (34) may be a unitary component consisting of an integrated threaded part (35) and activation part (16).

In the illustrated embodiment, the threaded part (35) is provided with a longitudinally extending helical thread (37) formed on the internal cylindrical surface. The helical thread (37) is threadedly engaged with the helical thread (32) of the unidirectional rotational coupling means (33) and thereby the piston rod (31) is releasably engaged with the drive sleeve (34).

The drive sleeve (34) has a plurality of features formed on the external surface designed to move axially within the guide slots (not shown) of the internal housing (7). These guide slots define the extent of permissible axial movement of the drive sleeve (34) with respect to the housing part (3). In the illustrated embodiment the guide slots also prevent rotational movement of the drive sleeve (34) relative to the main housing part (3).

The activation part (16) of the drive sleeve (34) has a plurality of grip surfaces (18) and a dispensing face (19).

The drive sleeve (34) is provided with a detent means that is designed to interact with a pawl means on the internal housing (7).

To increase intuitiveness of the operation of the device, the main housing part (3) may be provided with an optional window aperture through which optional graphical status indicators, provided on the drive sleeve (34), can be viewed.

Operation of the drug delivery device in accordance with the present invention will now be described.

To set a dose a user grips the grip surfaces (18) of the drive sleeve (34). The user then pulls the drive sleeve (34) in a proximal direction away from the main housing part (3).

The piston rod (31) is prevented from moving proximally by the part threads of the threaded circular opening (8) of the internal housing (7). As the drive sleeve (34) travels in the proximal direction relative to the piston rod (31), the unidirectional rotational coupling means (33) rotates with respect to the piston rod (31) by virtue of the engagement of the helical thread (32) of unidirectional rotational coupling means (33) with the helical thread (37) of the drive sleeve (34).

The proximal travel of the drive sleeve (34) is limited by the guide slots (not shown) of the internal housing (7). Visual feedback regarding dose setting may optionally be indicated by a graphical status indicator, provided on the drive sleeve (34), which can be viewed through a window aperture in the main housing part (3).

When the dose has been set, the user may then dispense this dose by depressing the dispensing face (19) of the activation part (16) of the drive sleeve (34). By this action the drive sleeve (34) is moved axially in the distal direction relative to the main housing part (3). As the helical thread (32) of unidirectional rotational coupling means (33) is engaged with the helical thread (37) of the drive sleeve (34) the unidirectional rotational coupling means (33) is caused to rotate with respect the drive sleeve (34) thus causing the unidirectional rotational coupling means (33) to engage with the piston rod (31).

The piston rod (31) is caused to rotate with respect to the internal housing (7) by the rotational movement of the unidirectional rotational coupling means (33). As the piston rod (31) rotates, the helical thread (30) of the piston rod (31) rotates within the threaded circular opening (8) of the internal housing (7) causing the piston rod (31) to move axially in the distal direction with respect to the internal housing (7).

The distal axial movement of the piston rod (31) causes the pressure foot (11) to bear against the piston (5) of the cartridge (4) causing a dose of medicament to be dispensed through the attached needle (not shown).

The distal travel of the drive sleeve (34) is limited by the guide slots of the internal housing (7). Visual feedback regarding dose dispensing may optionally be indicated by a graphical status indicator, provided on the drive sleeve (34), which can be viewed through a window aperture in the main housing part (3).

Examples 3A to 3E

The examples 3A to 3E refer to different embodiments of the drive mechanism for a drug delivery device according to the present invention comprising different non return features which prevent rotation of the piston rod during dose setting when the drive sleeve is moved proximally, thereby preventing proximal movement of the piston rod.

Figure 5A:
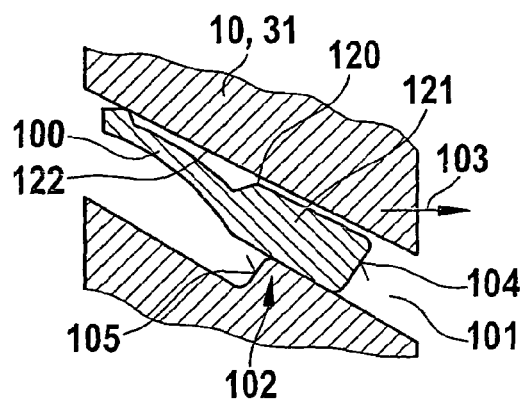
FIGS. 5a and 5b show schematically a first design of non-return features for a drive mechanism according to the present invention.
Figure 5B:
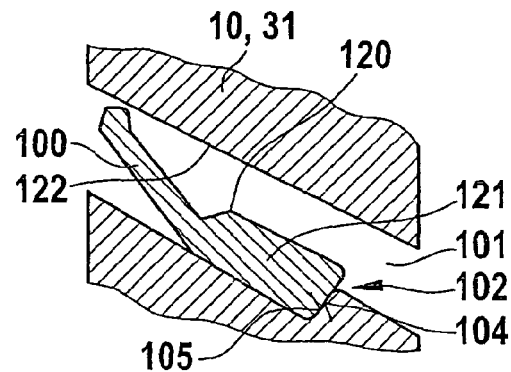

The non return features as shown schematically in FIGS. 5a and 5b (example 3A) are based upon at least one arm 120 with a flexible region 100 and a solid region 121 which is axially engaged by a step 102 in a helical groove 101 on the piston rod 10, 31 each time the dispensing of a dose is completed.

In the context of this application the feature of "axially engaging" shall mean that the engagement is achieved by an essentially axial movement of at least one of the two engaging components.

The arm 120 is connected to a part of the drug delivery device which does not move axially and does not rotate with respect to the main housing 3. Preferably the arm 120 is part of an internal housing 7 or of the main housing 3, most preferably the arm 120 is a thread form inside of the opening 8 of the internal housing 7. In a preferred embodiment of the present invention the arm 120 is in constant engagement with the helical groove 101 on the piston rod 10, 31.

During the dispensing action the piston rod 10, 31 rotates with respect to the housing 3 (the rotation being illustrated by the arrow 103 in FIG. 5a) and is at the same time moved distally (downwards in FIG. 5a), such that the helical groove 101 winds along the arm 120. FIG. 5a shows the arm 120 in a flexed position right before the end of dose. The arm 120 is biased such that it applies an axial force to the proximal side 122 of the helical groove 101 so that the step 102 in the helical groove 101 of the piston rod 10, 31 'drops over' the solid region 121 of the arm 120 when the step 102 is reached at the end of a dispensing action. In order to achieve this engagement between the arm 120 and the step 102 the biased arm 120 applies an axial force in the proximal direction to the piston rod 10, 31 thereby moving the piston rod proximally into engagement with the solid region 121 of the arm 120. In this relaxed position (see FIG. 5b) the end surface 104 of the arm 120 abuts an abutment surface 105 of the step 102, thereby preventing back rotation of the piston rod 10, 31 (in the direction opposite to arrow 103 in FIG. 5) when the drive sleeve 14, 34 moves distally during dose setting.

Figure 6A:
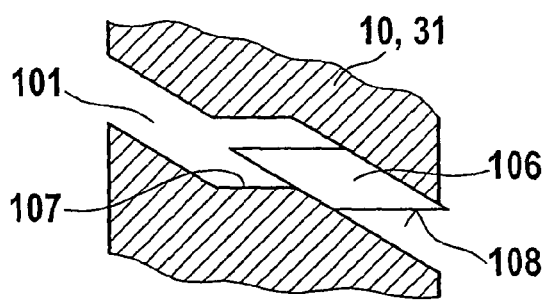
FIGS. 6a and 6b show schematically a second design of non-return features for a drive mechanism according to the present invention.
Figure 6B:
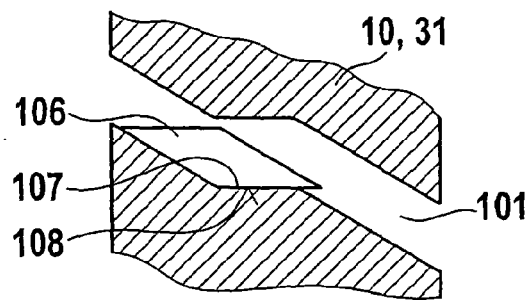

The non return features as shown schematically in FIGS. 6a and 6b (example 3B) are based upon at least one engaging element 106 with a cross section in the form of essentially a parallelogram which reaches a section with a smaller helix angle, in the shown case a flat section 107, in a helical groove 101 on the piston rod 10, 31 each time the dispensing of a dose is completed.

The engaging element 106 (which is preferably non-flexible) is connected to a part of the drug delivery device which does not move axially and does not rotate with respect to the main housing 3. Preferably the engaging element 106 is part of an internal housing 7 or of the main housing 3, most preferably the engaging element 106 is a thread form inside of the opening 8 of the internal housing 7. In a preferred embodiment of the present invention the engaging element 106 is in constant engagement with the helical groove 101 on the piston rod 10, 31.

During the dispensing action the piston rod 10, 31 rotates with respect to the housing 3 and is at the same time moved distally, such that the helical groove 101 winds along the engaging element 106. FIG. 6a shows the engaging element 106 in a first position right before the end of dose. The engaging element 106 is positioned next to a flat section 107 in the helical groove 101 of the piston rod 10, 31. When the step 102 is reached at the end of a dispensing action, the end surface 108 of engaging element 106 abuts the flat surface in the flat section 107 of the helical groove 101 (see FIG. 6b), thereby preventing back rotation of the piston rod 10, 31 when the drive sleeve 14, 34 moves distally during dose setting.

The advantage of these non-return features are that the parts containing the flat section 107 and the at least one engaging element 106 with a cross section in the form of a parallelogram are easy to mould.

The non-return features according to examples 3A or 3B can be combined with additional non-return features, e.g. according to examples 3C or 3D.

The non-return features as shown schematically in FIG. 7 (example 3C) are based upon at least one (preferably non-flexible) engaging element 109 which blocks movement of one of a plurality of raised sections 110 on the outer surface of the piston rod 10, 31 in at least one direction during the setting of a dose (when the drive sleeve 14, 34 is moved proximally without rotating with respect to the housing 3) and which can pass between the raised sections 110 during dispensing of a dose (when the drive sleeve 14, 34 is moved distally without rotating and the piston rod 10, 31 is rotated and moved distally with respect to the housing 3). At least one row of (preferably equidistant) raised sections 110 is preferably aligned in a longitudinal direction on the outer surface of the piston rod 10, 31. Preferably three or five longitudinal rows of equidistant raised sections 110 are provided on the circumference of the piston rod 10, 31.

The engaging element 109 is connected to a part of the drug delivery device which moves axially, but does not rotate with respect to the main housing 3 during dose setting. Preferably the engaging element 109 is part of the drive sleeve 14, 34 or of a component which is connected to the drive sleeve 14, 34, e.g. an insert. In a preferred embodiment of the present invention the engaging element 109 is at least one lug (preferably with a cross section in the form of a parallelogram) protruding inwards on the inside diameter of the drive sleeve 14, 34.

In FIG. 7 the engaging element 109 is shown in three different positions which are numbered 1, 2 and 3. During dose setting, the engaging element 109 moves (with the drive sleeve 14, 34) in the direction from position 1 to position 3 with respect to the piston rod 10, 31. In position 3 the dispensing of the dose can be started. In position 2 the piston rod 10, 31 is prevented from rotating backwards by the abutment of a side wall 111 of the engaging element 109 and an adjacent side wall 112 of a raised section 110. In position 1 the piston rod 10, 31 has just completed the dispensing of a dose and engaging element 109 has screwed forwards in a distal direction on a helical path through a gap 113 between two successive raised sections 110.

Figure 8B:
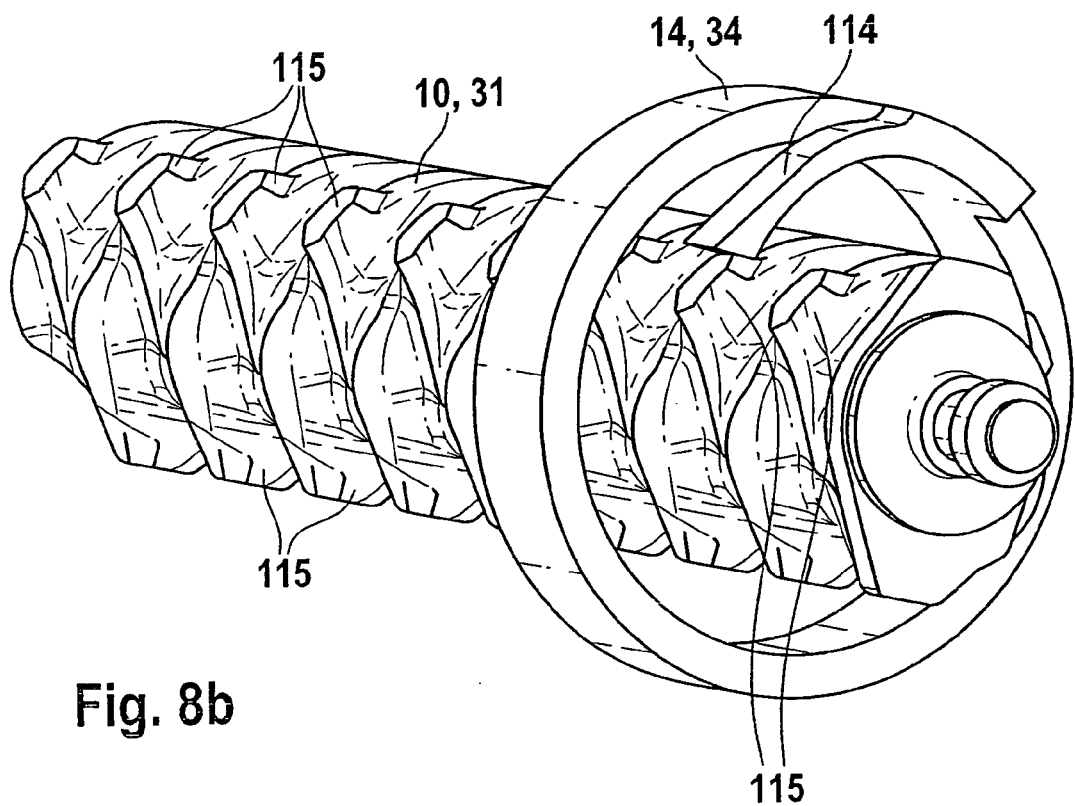

The non-return features as shown schematically in FIGS. 8a and 8b (example 3D) are based upon a unidirectional coupling between the piston rod 10, 31 and a non-rotating component of the drug delivery device, e.g. the housing 3 or the drive sleeve 14, 34. According to a preferred embodiment of the present invention the unidirectional coupling comprises at least one ratchet arm which is connected to the non-rotating component of the drug delivery device and comprises engaging sections on the outer surface of the piston rod 10, 31 which are engaged by the ratchet arm when a dose of medication has been dispensed by the drug delivery device. In the context of this application a "ratchet arm" shall mean an engaging feature which is flexibly connected to another component.

An engaging section on the outer surface of the piston rod 10, 31 can e.g. be a section containing a recess with an edge which is engaged by the ratchet arm or a raised section with an edge which is engaged by the ratchet arm. According to a preferred embodiment of the present invention at least one row of (preferably equidistant) engaging sections is aligned in a longitudinal direction on the outer surface of the piston rod 10, 31. Preferably three or five longitudinal rows of equidistant engaging sections are provided on the circumference of the piston rod 10, 31.

In the embodiment as shown in FIGS. 8a and 8b a ratchet arm 114 is connected to the drive sleeve 14, 34 and engages one of a plurality of raised sections 115 on the outer surface of the piston rod 10, 31 at the end of dose delivery. This engagement is shown in the figures, where a blocking surface 116 of the ratchet arm 114 abuts an abutment surface 117 of a raised section 115. In this position (in which a dose can be set by moving the drive sleeve 14, 34 proximally without rotation with respect to the (not shown) housing 3) a rotation of the piston rod 10, 31 with respect to the drive sleeve 14, 34 is prevented in a first direction by the abutment of surfaces 116, 117. The ratchet arm 114 is biased in the direction of the outer surface of the piston rod 10, 31.

During dose delivery, when the drive sleeve 14, 34 moves distally without rotation with respect to the housing 3 and the piston rod 10, 31 rotates in a second direction and moves distally with respect to the housing 3, the ratchet arm 114 allows the rotation of the piston rod 10, 31 in the second direction. During this rotation of the piston rod 10, 31, the ratchet arm 114 slides over the outer surface of the piston rod 10, 31 until it slides over the next raised section 115 and moves into engagement with this next raised section 115 at the end of dose delivery.

The non-return features according to example 3D can be combined in a drive mechanism for a drug delivery device according to the present invention with additional non-return features, e.g. according to example 3C. When the non-return features according to examples 3C and 3D are combined in the same drive mechanism, a single set of raised sections on the outer surface of the piston rod 10, 31 can take over the function of both described sets of raised sections 110 and 115 in examples 3C and 3D.

The non return features as shown schematically in FIGS. 9a to 9d (example 3E) are based upon at least one guiding feature of the drive sleeve which is designed to longitudinally guide a raised element on the outer surface of the piston rod during the setting of a dose to prevent rotation of the piston rod.

Figure 9A:
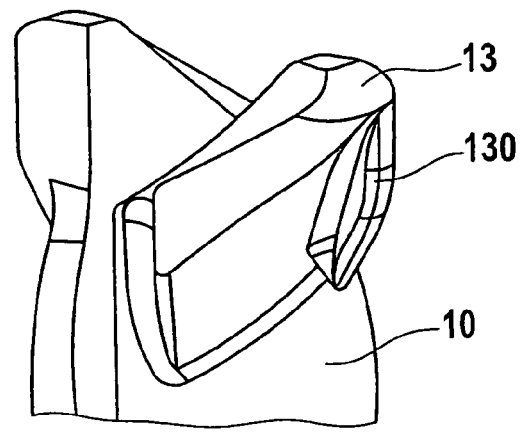
FIGS. 9a to 9d show a fifth design of non-return features for a drive mechanism according to the present invention.
Figure 9B:
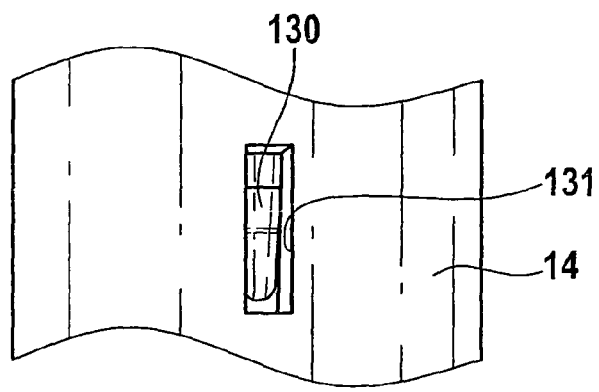
Figure 9C:
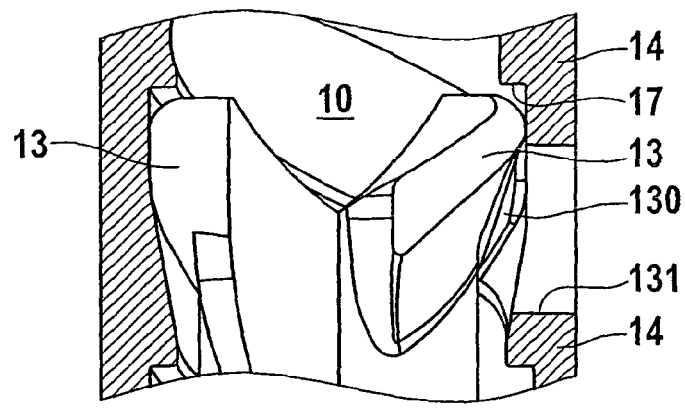
Figure 9D:
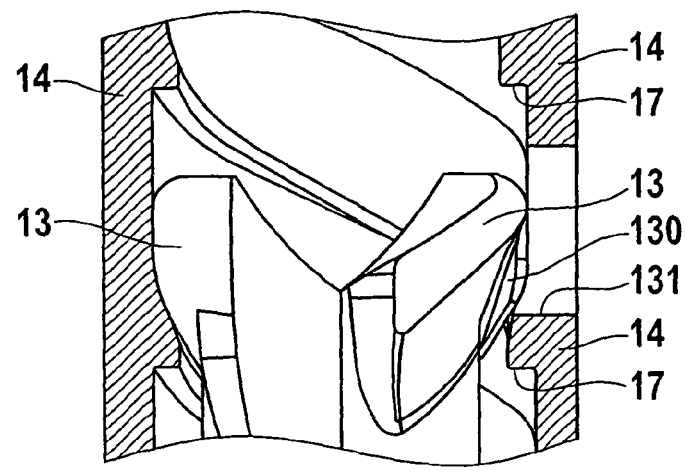

Preferably the guiding feature 131 is a narrow aperture which goes through the drive sleeve wall and which extends with a defined length in the longitudinal direction. The raised element 130 is preferably (as shown in FIG. 9a) a rib on the flexible arms 13 of a piston rod 10 according to the embodiment as shown in FIGS. 1 and 2.

During dose setting (see FIG. 9d), the drive sleeve 14 moves proximally with respect to the housing 3 without rotating. When the drive sleeve 14 is pulled back, the rib 130 on the flexible arms 13 of the piston rod 10 engages with the aperture 131 in the drive sleeve 14 to prevent relative rotation between the two parts. This engagement can also be seen in FIG. 9b. During the proximal movement of the drive sleeve 14 the piston rod 10 does not move and the aperture 131 therefore moves proximally with respect to the rib 130 which is thereby guided along the length of the aperture 131. The length of the aperture 131 is preferably adapted such that the piston rod 10 is prevented from relative rotation until it clicks back into position ready for the dispensing of the subsequent dose.

During the dispensing action (see FIG. 9c) the piston rod 10, rotates with respect to the (not shown) housing 3 and is at the same time moved distally. Therefore the rib 130 on the flexible arms 13 also screw rotates down the helical thread 17 of the drive sleeve 14 moving out of alignment with the first aperture and into alignment with another similar aperture at the end of the dispensing action.

The non-return features according to example 3E can be combined with other non-return features, e.g. one or more of the non-return features described above.

The invention claimed is:

1. A drive mechanism for use in a drug delivery device comprising:
a housing having a proximal and distal end;
a drive sleeve non-rotatable with respect to said housing;
a piston rod engaged with the said drive sleeve optionally by engagement means; wherein the said piston rod further comprises a distal helical thread portion threadedly engaged with the said housing and a means located at the proximal end of the said piston rod for releasable engagement to the said drive sleeve;
characterized in that,
a) when the said drive sleeve moves proximally without rotating with respect to the said housing the said piston rod does not move with respect to the said housing;
b) when the said drive sleeve moves distally the said piston rod rotates with respect to the said housing so that a force is transferred in the longitudinal direction to the distal end of the said drug delivery device.

2. A drug delivery device comprising the drive mechanism as defined in claim 1.

3. Use of a drug delivery device as defined in claim 2 for dispensing a medicinal product.

4. The use of a drug delivery device according to claim 3 for dispensing a pharmaceutical formulation comprising an active compound selected from the group consisting of insulin, growth hormone, low molecular weight heparin, their analogues, and their derivatives.

5. The drug delivery device according to claim 2, which is a pen-type device.

6. The drug delivery device according to claim 2, which is an injector-type device.

7. The drug delivery device according to claim 2, which comprises a needle.

8. The drug delivery device according to claim 2, which is a needle-free device.

9. The drive mechanism according to claim 1, comprising non-return features which prevent rotation of the piston rod at least in one direction with respect to the housing when the drive sleeve moves proximally with respect to the housing.

10. The drive mechanism according to claim 9, wherein the non-return features comprise an engaging feature which is designed to engage a stopping feature on the piston rod.

11. The drive mechanism according to claim 10, wherein the engaging feature is at least one feature selected from the group consisting of
a) at least one arm with a flexible section which is in constant engagement with a helical groove on the piston rod and which is designed to axially engage a step in the helical groove which is the stopping feature,
b) at least one engaging element with a cross section of essentially a parallelogram in constant engagement with a helical groove on the piston rod which is designed to engage a section in the helical groove with a smaller helix angle which is the stopping feature,
c) at least one non-flexible engaging element which is connected to the drive sleeve which is designed to abut at least one of a plurality of raised sections on an outer surface of the piston rod which is the stopping feature,
d) at least one ratchet arm which is connected to the drive sleeve or the housing and which is designed to engage at least one of a plurality of engaging sections on an outer surface of the piston rod which is the stopping feature and
e) at least one guiding feature of the drive sleeve which is designed to longitudinally guide a raised element on the outer surface of the piston rod which is the stopping feature.

12. The drive mechanism according to claim 1, wherein the said means located at the proximal end of the said piston rod for releasable engagement to the said drive sleeve consists of one or more flexible regions.

13. The drive mechanism according to claim 12, wherein the said one or more flexible regions are releasably engaged with a helical thread on the said drive sleeve.

14. The drive mechanism according to claim 1, wherein the said means located at the proximal end of the said piston rod for releasable engagement to the said drive sleeve consists of unidirectional rotational coupling means.

15. The drive mechanism according to claim 14, wherein the said unidirectional rotational coupling means are engaged with a helical thread on the said drive sleeve.

16. An assembly for use in a drug delivery device comprising the drive mechanism as defined in claim 1.

17. A method of manufacturing a drug delivery device, comprising the step of providing a drive mechanism as defined in claim 1.

18. A drive mechanism for a delivery device comprising:
a housing having a proximal and distal end;
a non-rotatable drive sleeve;
a piston rod comprising a distal thread and a proximal thread, the proximal thread of the piston rod threadedly engaged with the drive sleeve and the distal thread of the piston rod threadedly engaged with the housing;
wherein
when the non-rotatable drive sleeve moves proximally, the piston rod does not rotate; and
when the non-rotatable drive sleeve moves distally, the piston rod rotates with respect to the housing so that a force is transferred in the longitudinal direction to the distal end of the said housing.

19. The drive mechanism of claim 18 wherein the drive mechanism is used to administer at least one pre-set dose of a medicinal product.

20. The drive mechanism of claim 18 wherein the distal thread and the proximal thread are oppositely disposed.

* * * * *